United States Patent
Dubut et al.

(10) Patent No.: US 10,752,573 B2
(45) Date of Patent: Aug. 25, 2020

(54) PROCESS FOR PRODUCING (METH)ACRYLIC ESTERS

(71) Applicant: Arkema France, Colombes (FR)

(72) Inventors: Fanny Dubut, Metz (FR); Marc Esch, Theding (FR); Coralie Graire, Grezieu-la-Varenne (FR); Benoit Riflade, Bazas (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 16/466,791

(22) PCT Filed: Dec. 7, 2017

(86) PCT No.: PCT/FR2017/053449
§ 371 (c)(1),
(2) Date: Jun. 5, 2019

(87) PCT Pub. No.: WO2018/104677
PCT Pub. Date: Jun. 14, 2018

(65) Prior Publication Data
US 2020/0079722 A1    Mar. 12, 2020

(30) Foreign Application Priority Data
Dec. 8, 2016 (FR) ..................................... 16 62132

(51) Int. Cl.
*C07C 67/03* (2006.01)
*B01J 19/00* (2006.01)
(Continued)

(52) U.S. Cl.
CPC ............ *C07C 67/03* (2013.01); *B01F 5/0615* (2013.01); *B01F 5/106* (2013.01); *B01J 19/0046* (2013.01);
(Continued)

(58) Field of Classification Search
None
See application file for complete search history.

(56) References Cited

U.S. PATENT DOCUMENTS 6,211,390 B1 * 4/2001 Peter ...................... C07C 67/58
                                                554/170
10,000,439 B2 * 6/2018 Riondel ................. C07C 67/54
(Continued)

FOREIGN PATENT DOCUMENTS

FR         2 811 986        1/2002
WO    WO-2014096648 A1 *    6/2014    ............. C07C 67/54

OTHER PUBLICATIONS

Alves, M. H. et al, "Polymer-supported titanate as catalyst for the transesterification of acrylic monomers" Comptes Rendus-Chimie, Elsevier, Paris, FR, vol. 13, No. 10.; Oct. 2010 (pp. 1301-1307), XP027298826, ISSN: 1631-0748 [extraite le Sep. 18, 2010].

*Primary Examiner* — Amy C Bonaparte
(74) *Attorney, Agent, or Firm* — Lynn B. Morreale

(57) ABSTRACT

This invention relates to a process for the continuous production of a (meth)acrylic ester by transesterification reaction between a C1-C4 light alkyl (meth)acrylate, with a heavy alcohol in the presence of a catalyst, characterised in that the flows feeding the reactor are introduced through a static mixer placed on a recirculation loop of the reactor. The use of a static mixer improves the selectivity of the reaction and consequently the overall productivity of (meth)acrylic ester synthesis process.

8 Claims, 2 Drawing Sheets

Figure 1:
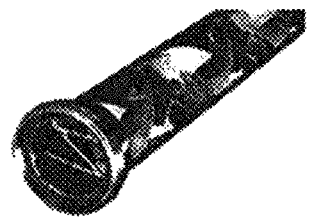

(51) Int. Cl.
*C07C 67/02* (2006.01)
*C07C 69/54* (2006.01)
*C07C 213/06* (2006.01)
*C07C 213/10* (2006.01)
*B01F 5/06* (2006.01)
*B01F 5/10* (2006.01)

(52) U.S. Cl.
CPC ............ *C07C 67/02* (2013.01); *C07C 213/06* (2013.01); *C07C 213/10* (2013.01); *B01J 2219/00033* (2013.01); *C07C 69/54* (2013.01); *Y02P 20/582* (2015.11)

(56) References Cited

U.S. PATENT DOCUMENTS

| | | |
|---|---|---|
| 2002/0133041 A1 | 9/2002 | Paul et al. |
| 2008/0161596 A1 | 7/2008 | Riondel et al. |
| 2014/0350291 A1 | 11/2014 | Paul et al. |
| 2015/0203436 A1 | 7/2015 | Riondel et al. |
| 2015/0315120 A1 | 11/2015 | Riondel et al. |
| 2016/0023985 A1 | 1/2016 | Riondel et al. |
| 2017/0267624 A1 | 9/2017 | Moreliere et al. |
| 2018/0009736 A1 | 1/2018 | Cabon et al. |

* cited by examiner

PROCESS FOR PRODUCING (METH)ACRYLIC ESTERS

CROSS-REFERENCE TO RELATED APPLICATIONS

This application is a national stage application under 35 U.S.C. § 371 of PCT/FR2017/053449, filed Dec. 7, 2017 which claims benefit to application FR 16 62132, filed Dec. 8, 2016.

TECHNICAL FIELD

The present invention relates to the production of (meth) acrylic esters by a continuous transesterification process and in particular, the production of N,N-dimethylaminoethyl acrylate (hereinafter referred to as ADAME).

The invention provides a process for producing a (meth) acrylic ester with improved productivity by transesterification of a light alkyl (meth)acrylate with a heavy alcohol. The improvement of the invention process is based on the optimisation of the reaction section, particularly at the level of the introduction of reagents and catalyst into the transesterification reactor.

PRIOR ART AND TECHNICAL PROBLEM

Industrial processes for the production of (meth)acrylic esters by transesterification involve a $C_1$-$C_4$ "short"-chain alkyl (meth)acrylate, called light alkyl (meth)acrylate or light (meth)acrylate which reacts with a "longer" carbon chain alcohol, called heavy alcohol, generally in the presence of a catalyst and polymerization inhibitors, according to the following general formula (1):

$$H_2C=C(R)COOR_1 + R_2OH \rightleftharpoons H_2C=C(R)COOR_2 + R_1OH \quad (1)$$

where R=H or $CH_3$; $R_1$ alkyl chain in $C_1$-$C_4$; $R_2OH$ heavy alcohol

In order to shift the equilibrium towards the formation of "long chain" alkyl (meth)acrylate, the light alcohol $R_1OH$ released during the reaction is continuously eliminated in the form of an azeotrope with excess light (meth)acrylate. Due to the presence of light alcohol, this azeotrope is advantageously recycled on the light (meth)acrylate production unit the synthesis of which is based on the direct esterification of (meth)acrylic acid with light alcohol.

The transesterification reaction is accompanied by side reactions producing impurities in the reaction medium, generally in the form of "heavy" compounds. The reaction medium is then subjected to a set of treatments aimed at recovering pure (meth)acrylic ester, and separating recoverable fractions.

For the sake of productivity, various studies have already focused on the recycling of fractions generated during purification, or on the treatment of "heavy" fractions capable of releasing noble products such as the reagents involved in the reaction. Such processes for upgrading noble products are for example described in document WO 2013/045786 or WO 2016/124837.

The overall economic balance of these industrial processes is strongly related to increasing the yield of raw materials, that is, the amount of reagents and catalyst necessary to obtain 1000 kg of final product.

The recycling of certain fractions generated during the purification treatment improves the raw material balance, but nevertheless requires a significant energy input.

There is therefore still a need to improve the productivity of the processes for producing (meth) acrylic esters by transesterification.

In patent document WO 2006/040470, it is proposed that the transesterification reaction be carried out in an equilibrium continuous displacement reactor, more precisely a plug-flow reactor composed of a baffled horizontal tube exchanger in which each compartment can be assimilated to a single perfectly stirred reactor. According to this method, it is possible to obtain a better conversion of the alcohol reagent, and a better selectivity of (meth)acrylic ester.

In patent document EP 1 219 587, the mixing of reagents passes in upflow mode through a cationic resin bed as catalyst in a recirculation loop which is associated with a stirred tank thereby mixing the reagents. This process relates in particular to the synthesis of (meth) acrylic esters by direct esterification.

Inventors have now discovered that by distributing the transesterification catalyst more efficiently and homogeneously within the reaction medium, it is possible to improve the selectivity of the reaction and consequently the overall productivity of a (meth)acrylic ester synthesis process.

SUMMARY OF THE INVENTION

Therefore, the object of this invention is a process for continuous production of a (meth)acrylic ester by transesterification reaction between a light alkyl (meth)acrylate selected from methyl (meth)acrylate and ethyl (meth)acrylate, with a heavy alcohol in the presence of a catalyst, characterised in that the flows feeding the reactor are introduced through a static mixer which is a pipe element comprising propellers or baffles or any other obstacle intended to increase turbulence, placed on a recirculation loop of reagents, catalyst and recycled flows upstream of the reactor.

"Flows feeding the reactor", refers to flows of pure products (reagents and catalyst) as well as flows recycled in the process.

"By the intermediary of a static mixer" indicates that flows are not introduced separately and directly into the reactor, for example using an immersion rod. According to the invention, flows are grouped into a single flow which passes through a static mixer consisting of a pipe element comprising propellers or baffles or any other obstacle intended to increase turbulence, in order to homogenise this flow before feeding the reactor.

According to the invention, the use of a static mixer to introduce raw materials and the catalyst into the reactor ensures better contact of the reactants with the catalyst and a better homogenization of the reaction medium. This prevents the formation of areas of high catalyst concentrations which are conducive to the generation of heavy by-products. These by-products are, for example, Michael adducts resulting from addition reactions on (meth)acrylic double bonds, or oligomers or polymers. The formation of zones of low catalyst concentrations which risk limiting the conversion of reagents is also avoided. A uniform kinetics of the conversion of reagents is then ensured.

The formation of (meth)acrylic ester is enhanced and consequently, the selectivity of transesterification reaction is improved. This causes a reduction in reagents and catalyst setting in the process.

According to the invention, the static mixer is a pipe element comprising propellers or baffles or any other obstacle intended to increase turbulence and thus to enhance the mixing of flows.

According to the invention, the static mixer is placed on a recirculation loop of reagents and catalyst and recycled flows upstream of the reactor.

According to one embodiment, the static mixer is placed upstream of the reactor reboiler.

According to one embodiment, the static mixer is placed downstream of the reactor reboiler.

According to one embodiment, the heavy alcohol is a primary or secondary linear or branched alcohol, comprising between 4 and 12 carbon atoms, which can comprise at least one nitrogen atom.

According to one embodiment of the invention, the heavy alcohol is an amino alcohol of formula (II):

wherein

A is an alkylene radical, linear or branched, in $C_1$-$C_5$ $R'_2$ et $R'_3$, which are identical or different from one another, each representing a $C_1$-$C_4$ alkyl radical.

The heavy alcohol can be for example N,N-dimethylaminoethanol (DMAE), N,N-diethylaminoethanol, N,N-dimethylaminopropanol.

According to a preferred embodiment of the invention, the amino alcohol is N,N-dimethylaminoethanol (DMAE), and the (meth) acrylic ester is N,N-dimethylaminoethyl acrylate (ADAME).

According to one embodiment of the invention, the heavy alcohol is an alcohol of formula $R_2OH$ wherein $R_2$ represents a linear or branched alkyl chain in $C_4$-$C_{12}$, preferably in $C_5$-$C_{12}$. The heavy alcohol can be primary or secondary.

The heavy alcohol is for example, 2-ethyl hexanol, 2-octanol or 2-propyl heptanol.

According to the invention, the light alkyl (meth)acrylate is selected from methyl (meth)acrylate and ethyl (meth) acrylate.

According to a preferred embodiment of the invention, the light alkyl (meth)acrylate is methyl acrylate or ethyl acrylate.

A second object of the invention is a process for the continuous production of a (meth)acrylic ester by transesterification reaction between a light alkyl (meth)acrylate, selected from methyl (meth)acrylate and (meth) ethyl acrylate, with a heavy alcohol in the presence of a catalyst, said method comprising at least the following steps:

a) feeding a reactor with a light alkyl (meth)acrylate, a heavy alcohol, a transesterification catalyst, and at least one polymerization inhibitor in a reactor, and subjecting the reaction mixture to transesterification conditions to form:
   i) a product mixture comprising the (meth)acrylic ester formed, the light alkyl (meth)acrylate and the unreacted heavy alcohol, the catalyst, the polymerization inhibitors and heavy by-products; and
   ii) an azeotropic mixture light alkyl (meth)acrylate/ light alcohol released;

b) distilling on a first distillation column of the mixture i) of products separating at the top, a flow consisting essentially of the desired (meth)acrylic ester and light products, and at the bottom, a heavy fraction essentially comprising the catalyst, the polymerization inhibitors and heavy by-products;

c) purifying said overhead flow with at least a second distillation column, making it possible to obtain the purified (meth)acrylic ester, and a light product stream which is recycled to the reaction;

d) passing at least a portion of said heavy foot fraction on a film evaporator separating traces of light compounds which are recycled to the feed of the first distillation column, the heavy residue being removed;

e) optionally recycling in the reactor at least a portion of said heavy foot fraction of the first distillation column or heavy residue formed in step d);

f) optionally recycling the azeotropic mixture ii) formed in step a), to the unit for producing the light alkyl (meth)acrylate;

g) optional thermal cracking of at least a portion of said heavy foot fraction of the first distillation column, or heavy residue formed in step d);

said process being characterised in that the flows feeding the reactor pass through a static mixer which is a pipe element comprising propellers or baffles or any other obstacle intended to increase turbulence, placed on a recirculation loop of the reactor.

According to one embodiment of the invention, the purification step c) is carried out using two serial distillation columns.

The invention is appropriately used for the production of N,N-dimethylaminoethyl (ADAME) acrylate by transesterification reaction between ethyl acrylate (EA) and N,N-dimethylaminoethanol (DMAE), the static mixer can be placed on a recirculation loop of the reactor upstream or downstream of the reactor reboiler.

Thus, the invention also relates to the use of a static mixer for homogeneously introducing raw materials and catalyst, and optionally recycled flows, into the reaction section of N,N-diethylaminoethyl (ADAME) acrylate production process by transesterification reaction between ethyl acrylate (EA) and N,N-dimethylaminoethanol (DMAE).

The invention will now be more fully described in the description which follows, and with reference to the following figures:

FIG. 1: illustration of a mixer usable according to the invention.

Figure 2:
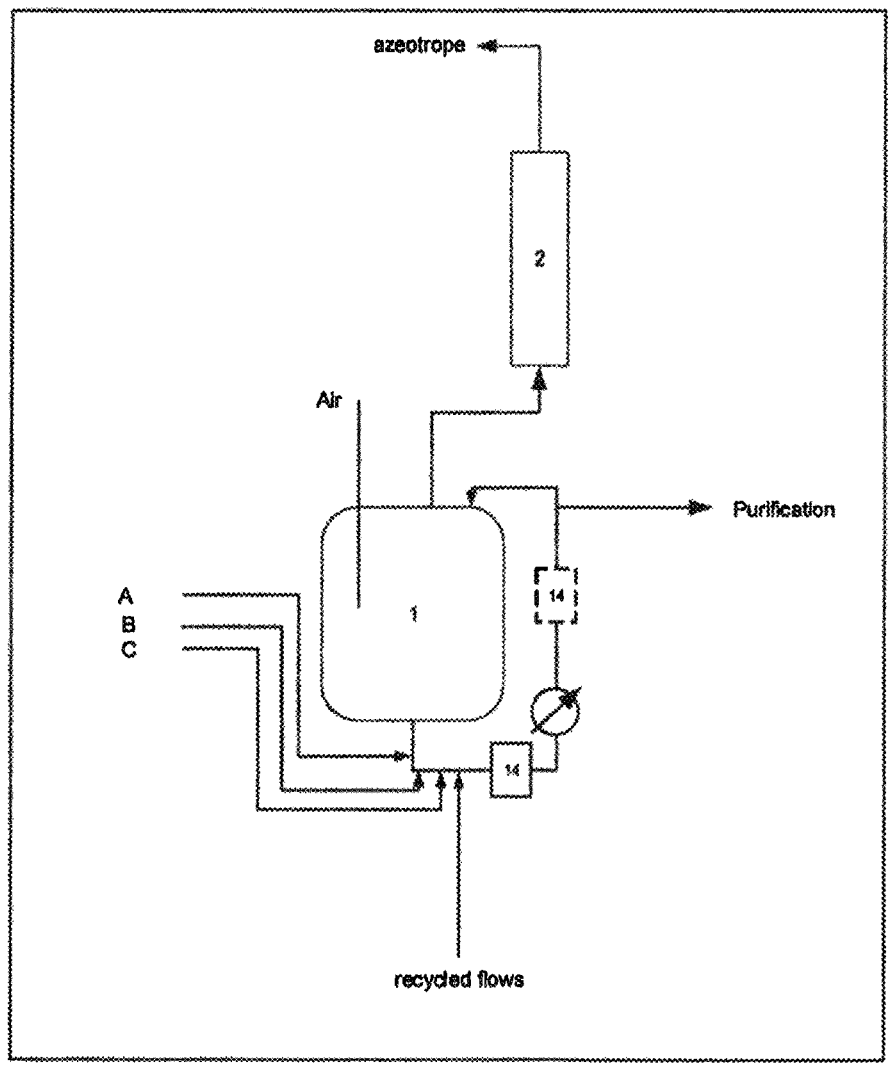

FIG. 2: diagram of a reaction section including the flow introduction mode in a transesterification reactor according to the invention.

Figure 3:
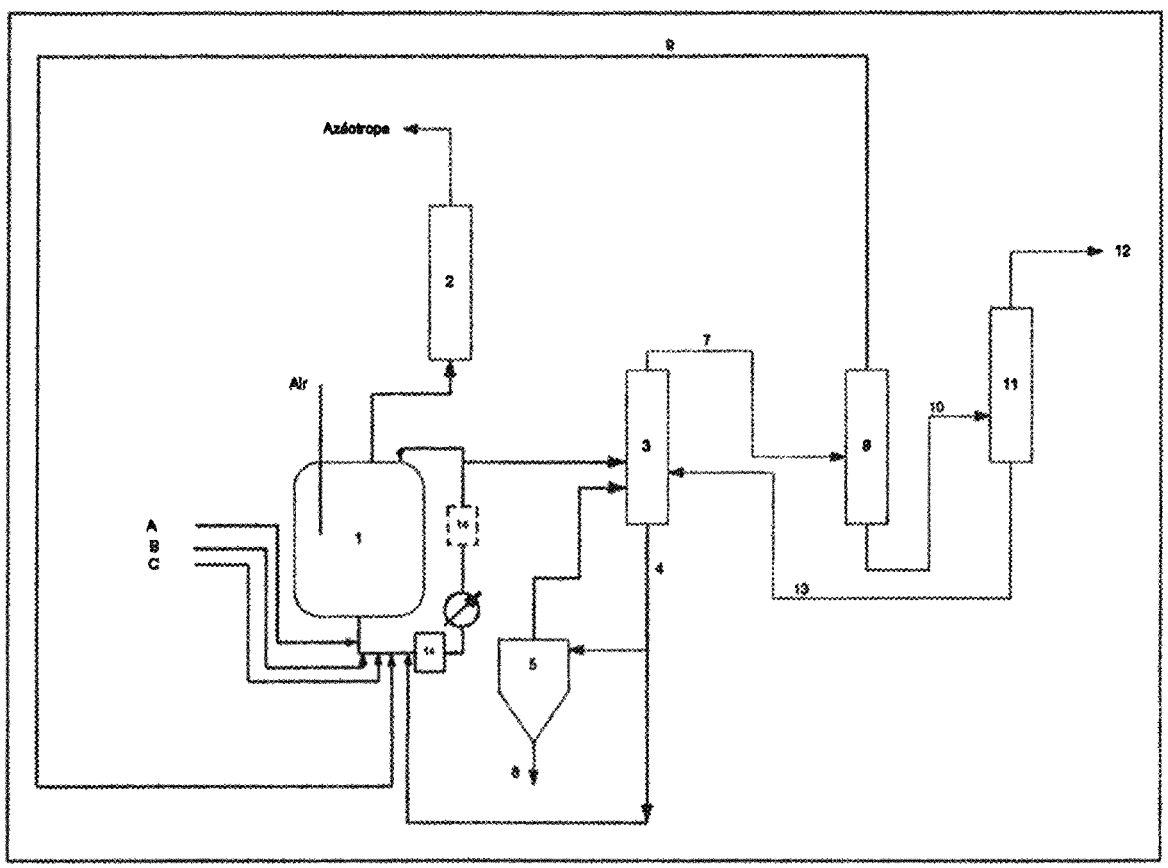

FIG. 3: schematic representation of a set-up adapted to implement the process of the invention.

DETAILED PRESENTATION OF THE INVENTION

In the processes of the prior art, the catalyst is introduced directly into the reactor, for example using an immersion rod, separated from the reactant flows feeding (as represented for example in patent documents WO 2013/110877; WO 2014/131970; FR 2 811986).

According to the figure illustrating purification using a single distillation column, of a reaction mixture resulting from a transesterification reaction, described in document WO2014/096648, the reagents and catalyst are introduced into the reactor as a single flow formed in a recirculation loop. However, the homogenisation of the reaction medium and the uniform kinetics of the conversion of reagents are not problems in this process which mainly concerns obtaining a final high purity product. It is therefore not suggested to place a static mixer in the recirculation loop.

According to the invention, the introduction of reagents and catalyst is optimised by using a static mixer in the recirculation loop of the reactor. Thus, it is ensured that the mixture of the reagents and the catalyst is properly carried out when it enters the reactor after the recirculation loop. The presence of overconcentration of the catalyst in the loop and reactor is avoided, and a better distribution of the catalyst is achieved in the reaction medium.

Recommended static mixers include those marketed for example by the CTMI company at St Avoid or by the Sulzer company.

FIG. 1 illustrates an example of a mixer adapted to the process according to the invention.

FIG. 2 shows a reaction section comprising a transesterification reactor 1 and a static mixer 14. An alkyl (meth) acrylate flow A and a heavy alcohol flow B, as well as a catalyst flow C are grouped into a single flow which passes through a static mixer 14 which is connected at the outlet to reactor 1. The thorough mixing of catalyst C with reagents A and B is carried out inside the static mixer, before being introduced into the reactor.

Static mixer 14 can be placed upstream or downstream of the reboiler in the recirculation loop of the reactor.

The formation of heavy by-products being minimized because of the absence of zones with high catalyst concentrations in the reactor, the reaction conditions can be adapted in order to optimise the reaction yield, mainly by increasing the residence time in the reactor to lead to an increase in raw material conversion rates, and consequently an improvement in raw material yield.

Transesterification reaction is generally carried out in reactor 1 at a pressure between 500 mm Hg (0.67105 Pa) and atmospheric pressure, preferably at a pressure of about 700 mm Hg, and temperature ranging from 70° C. to 130° C., preferably 100° C. to 120° C.

The light alkyl (meth)acrylate/heavy alcohol molar ratio can range from 1 to 3, preferably, it fails between 1.3 and 1.8.

The transesterification reaction is carried out in the presence of a catalyst according to methods well known to the person skilled in the art. For example, the transesterification catalyst can be a tetraalkyl titanate in solution in an alcohol such as the heavy alcohol used in the reaction, preferably tetraethyl titanate in solution in the heavy alcohol; the catalyst can also be a titanate of the heavy alcohol, for example tetra (dimethylaminoethyl) titanate, or tetra (2-ethylhexyl) titanate.

The reaction is carried out in the presence of one or more polymerization inhibitors which are introduced into the reactor at a rate of 1000 to 5000 ppm relative to the crude reaction mixture. The polymerisation inhibitors that can be used include, for example, phenothiazine, hydroquinone, hydroquinone monomethyl ether, diterbutyl para-cresol (BHT), TEMPO (2,2,6,6-tetramethyl-1-piperidinyloxy), di-tert-butylcatechol, or TEMPO derivatives, such as 4-hydroxy TEMPO (4-OHTEMPO), alone or mixtures thereof in all proportions.

The residence time in the reactor is generally between 5 and 8 hours.

FIG. 3 illustrates a set-up adapted for the implementation of a continuous process for producing (meth) acrylic esters by transesterification from light alkyl (meth) acrylates, and heavy alcohols as defined in the invention.

This set-up is described more particularly, but not limited to, the case of the production of ADAME by transesterification from EA and DMAE, which comprises steps (a) to (g) as defined in the process according to the invention.

FIG. 3 shows a transesterification reactor 1, a reboiler and a static mixer 14 which can be placed upstream or downstream of the reboiler in a recirculation loop of the reactor.

Reagents A and B (EA and DMAE) and a transesterification catalyst C are introduced into the recirculation loop of the reactor, to ensure they are homogeneously mixed before being introduced into reactor 1. Recycled flows from the purification section can also be introduced in the recirculation loop.

According to a first step (a), the transesterification reaction between AE and DMAE is carried out in reactor 1 in the presence of catalyst C, preferably tetraethyl titanate, and polymerization inhibitors. To reactor 1 is attached a distillation column 2 which serves to remove the light alcohol formed (ethanol) as it is being formed and thus to shift the reaction equilibrium in the direction of formation of ADAME.

The reaction mixture comprises the ADAME formed, unreacted EA and DMAE, catalyst C, polymerisation inhibitors, Michael adducts resulting from addition reactions on (meth) acrylic double bonds, and other heavy compounds such as oligomers or polymers.

According to step (b) of the process, the reaction mixture is distilled on a distillation column (tailing column 3). At the top of column 3, a flow 7 is recovered devoid of most of the catalyst and polymerisation inhibitors and comprising the ADAME produced and light compounds such as DMAE and EA, with a minor fraction of Michael adducts and heavy products.

At the bottom of column 3 a heavy fraction 4 is recovered comprising the catalyst, polymerisation inhibitors, Michael adducts and heavy compounds, with a minor fraction of ADAME and DMAE and traces of light compounds.

According to step (c) of the process, flow 7 is subjected to purification which is carried out using distillation column 8, whose top flow 9 comprising the unreacted reagents is recycled to the reaction, with the bottom flow 10 directed to a distillation column 11 making it possible to obtain at the top the purified ADAME 12, and at the bottom a flow 13 rich in inhibitors which is recycled in the crude reaction mixture flow feeding the first column 3.

According to step (d) of the process, the heavy fraction 4 from the bottom of column 3 which contains mainly the catalyst is partly concentrated on a film evaporator 5 which enables the separation of the traces of light compounds which are then recycled to the feeding of column 3, with the heavy residue 6 being removed or sent to a cracking unit (not shown), or optionally recycled to the reaction.

The heavy fraction 4 from the bottom of column 3 can be partly recycled to the reaction (step e).

This invention thus provides a simple solution to implement on existing (meth) acrylic ester synthesis plants and leading to improved productivity and selectivity. The process according to the invention also minimizes the size and energy of equipment for separation/recycling of flows generated during the purification of the reaction medium.

The following examples illustrate the present invention without limiting its scope.

EXPERIMENTAL PART

Example 1

On an industrial unit producing ADAME from ethyl acrylate (EA) and N,N-dimethylaminoethanol (DMAE), the catalyst (ethyl titanate solution in DMAE) is introduced to the reaction through an immersion rod, separated from the reactant flows, directly into the reactor.

A static mixer was placed on the recirculation loop of the reactor as shown in FIG. 2, to replace the injection lance. The reactants and catalyst are introduced into the reactor through this mixer.

The reaction conditions, temperature, residence time and flow rate were not changed.

DMAE alcohol and catalyst setting, as well as the heavy quantity exiting the unit (fraction 6 in FIG. 3) for one tonne of ADAME produced, were determined over a period of 8 months before and after adding the mixer.

The test results indicated that the installation of a static mixer replacing immersion rods to introduce the reagents and catalyst led to:

A reduction of 3 kg/t of catalyst
A reduction of 2 kg/t of DMAE

The improvement of the AE yield induced by the addition of the mixer has not been quantified.

In addition, the heavy quantity exiting the unit could be reduced by a mass of more than 10%.

The facility productivity of the facility has globally increased.

Example 2

In order to evaluate the quality of reagent mixing within a reactor, a CFD (Computational Fluid Dynamics) simulation method was applied. This method makes it possible to demonstrate low mixing zones, providing a heterogeneity of the residence times which induces a degradation of the conversion of reagents and selectivity of chemical reactions. Two approaches were used to highlight the advantages of the method according to the invention:

1) Visualization of the Flows and the Mixing of Reagents in a Reactor

Particles course simulating EA and DMAE compounds from their introduction into a reactor through immersion rods was visualized. A heterogeneity of the routes followed by these reagents could be demonstrated, and the direction followed by each of the reagents was not moving towards an immediate mixing.

In addition, according to the arrangement chosen in the reactor for the DMAE introduction rod, a high heterogeneity of its concentration in the reactor was observed by generating enriched zones and depleted zones of DMAE reagent. Introduction rods act as obstacles and also constitute sources of interference of reagent flows.

The arrangement of the rods for introducing reagents into the reactor must be subject to optimisation studies in order to minimize these problems.

According to the invention, the formation of zones with over- or under-concentration of reagents is prevented by ensuring a perfect mixture of the reagents using a static mixer upstream of the reactor, on the recirculation loop. The conversion of the reagents is then done according to uniform kinetics, and the formation of Michael-type by-products is minimized.

2) Determination of the Effective Volume in the Reactor

The injection of particles of the two reagents, EA and DMAE, as well as the catalyst, was simulated in a tank, on the one hand from injection cannulas, and on the other from the free surface receiving the flow of a mixing of reagents and catalyst carried out upstream. The number of injection time steps (one step is equal to 2 ms) was varied to check the rate at which the reagents spread in the tank. At the end of the injection, the number of cells crossed by all 3 compounds was counted, in order to calculate the corresponding volume representing the effective volume of the reactor.

The comparison of the 2 injection systems, expressed as the percentage of the effective volume in relation to the reactor volume, is shown in the following table.

| Method of introducing reagents and catalyst | Immersion rods | Upstream mixer |
|---|---|---|
| 5000 pas time | 0% | 27.8% |
| 10000 pas | 0.3% | 93.3% |
| 14000 pas | 50% | 99% |

With the process according to the invention, an instantaneous and homogeneous mixture of the reagents is observed and the reagents fill up the entire reactor volume more rapidly.

The invention claimed is:

1. A process for continuous production of a (meth)acrylic ester, said process comprising a homogeneous transesterification reaction between a light alkyl (meth)acrylate selected from the group consisting of methyl (meth)acrylate, methyl acrylate, ethyl (meth)acrylate and ethyl acrylate, with a heavy alcohol in the presence of a homogeneous transesterification catalyst and polymermization inhibitor using a reactor comprising a static mixer, a reactor reboiler, and a recirculation loop for carrying reagents, catalyst, and recycled flows which joins an outlet of the reactor to an inlet of the reactor through the reboiler, wherein all flows feeding the reactor are introduced through the static mixer which is a pipe element with propellers or baffles or other obstacles to increase turbulence, placed on the recirculation loop, and upstream or downstream of the reactor reboiler, such that a combined flow of reagents, catalyst, and recycled flows passes through the static mixer before entering the reactor.

2. The process according to claim 1 wherein the heavy alcohol is a linear or branched, primary or secondary alcohol comprising between 4 and 12 carbon atoms, optionally comprising at least one nitrogen atom.

3. The process according to claim 1 wherein the heavy alcohol is an amino alcohol of formula (II):

$$\text{HO-A-N(R'}_2\text{)(R'}_3\text{)} \tag{II}$$

wherein
A is a $C_1$-$C_5$ linear or branched alkylene radical
$R'_2$ and $R'_3$, which are identical or different from one another, each represent a $C_1$-$C_4$ alkyl radical.

4. The process according to claim 1 wherein the heavy alcohol is N,N-dimethylaminoethanol (DMAE), N,N-diethylaminoethanol, or N,N-dimethylaminopropanol.

5. The process according to claim 1 wherein the heavy alcohol is a primary or secondary alcohol of formula $R_2OH$ wherein $R_2$ represents a $C_4$-$C_{12}$ linear or branched alkyl chain.

6. The process according to claim 1 wherein the heavy alcohol is 2-ethyl hexanol, 2-octanol or 2-propyl heptanol.

7. A process for the continuous production of a (meth)acrylic ester by a homogeneous transesterification reaction between a light alkyl (meth)acrylate selected from the group consisting of methyl (meth)acrylate, methyl acrylate, ethyl (meth)acrylate, and ethyl acrylate with a heavy alcohol in the presence of a homogeneous transesterification catalyst and polymerization inhibitor, said method comprising at least the following steps:
a) feeding a reactor with the light alkyl (meth) acrylate, the heavy alcohol, the transesterification catalyst, and at least one polymerization inhibitor, and subjecting the reaction mixture to transesterification conditions to form:

i) a product mixture comprising the (meth) acrylic ester formed, the light alkyl (meth)acrylate and the unreacted heavy alcohol, the catalyst, the polymerization inhibitors and heavy by-products; and ii) an azeotropic mixture of the light alkyl (meth) acrylate and the light alcohol released from the light alkyl(meth)acrylate during transesterification;

b) distilling, in a first distillation column, the product mixture i) of step a), and separating at the top, a stream consisting essentially of the desired (meth) acrylic ester and light products, and at the bottom, a heavy fraction comprising the catalyst, the polymerization inhibitors and heavy by-products;

c) purifying said overhead stream with at least a second distillation column, to obtain a purified (meth)acrylic ester, and a light product stream which is recycled to the reaction;

d) passing at least a portion of said heavy bottoms fraction to a film evaporator and separating traces of light compounds therefrom, wherein said light compounds are then recycled to the feed of the first distillation column, and the heavy residue is removed;

e) optionally recycling at least a portion of said heavy bottoms fraction of the first distillation column or the heavy residue formed in step d) to the reactor;

f) optionally recycling the azeotropic mixture ii) formed in step a), to a unit for producing light alkyl (meth) acrylate;

g) optional thermal cracking of at least a portion of said heavy bottoms fraction of the first distillation column, or heavy residue formed in step d);

wherein the reactor comprises a static mixer, a reactor reboiler, and a recirculation loop for carrying reagents, catalyst, and recycled flows which joins an outlet of the reactor to an inlet of the reactor through the reboiler, wherein all flows feeding the reactor described in steps a) and e) pass through a static mixer which is a pipe element with propellers or baffles or other obstacles to increase turbulence, placed on the recirculation loop of the reactor, such that a combined flow of reagents, catalyst, and recycled flows passes through the static mixer before feeding into the reactor.

8. The process according to claim 7, wherein the (meth) acrylic ester is N,N-dimethylaminoethyl acrylate, the light alkyl (meth)acrylate is ethyl acrylate and the heavy alcohol is N,N-dimethylaminoethanol.

\* \* \* \* \*